United States Patent
Grant

(12) United States Patent Grant

(10) Patent No.: US 11,771,374 B2
(45) Date of Patent: Oct. 3, 2023

(54) CRANIAL IMPLANT

(71) Applicant: Strathspey Crown, LLC, Newport Beach, CA (US)

(72) Inventor: Robert Edward Grant, Laguna Beach, CA (US)

(73) Assignee: Ceyeber Corp., Newport Beach, CA (US)

( * ) Notice: Subject to any disclaimer, the term of this patent is extended or adjusted under 35 U.S.C. 154(b) by 282 days.

(21) Appl. No.: 17/106,950

(22) Filed: Nov. 30, 2020

(65) Prior Publication Data

US 2022/0167923 A1    Jun. 2, 2022

(51) Int. Cl.
*A61B 5/00* (2006.01)
*G16H 20/70* (2018.01)

(52) U.S. Cl.
CPC .......... *A61B 5/6868* (2013.01); *A61B 5/0031* (2013.01); *A61B 5/486* (2013.01); *A61B 5/4836* (2013.01); *A61B 5/72* (2013.01); *A61B 5/743* (2013.01); *G16H 20/70* (2018.01)

(58) Field of Classification Search
CPC ... A61B 5/6868; A61B 5/0031; A61B 5/4836; A61B 5/486; A61B 5/72; A61B 5/743; A61B 5/165; A61B 5/37; A61B 5/375; A61B 5/7278; A61B 5/742; G16H 20/70; G16H 40/63
See application file for complete search history.

(56) References Cited

U.S. PATENT DOCUMENTS

| | | | |
|---|---|---|---|
| 9,030,495 B2 * | 5/2015 | McCulloch | G09G 5/377 715/708 |
| 9,483,117 B2 | 11/2016 | Karkkainen | |
| 9,662,199 B2 | 5/2017 | Grant | |
| 10,299,912 B2 | 5/2019 | Grant | |
| 10,467,992 B2 | 11/2019 | Deering | |
| 2010/0234942 A1 | 9/2010 | Peyman | |
| 2013/0009993 A1* | 1/2013 | Horseman | G16H 40/63 345/633 |
| 2013/0063550 A1 | 3/2013 | Ritchey | |
| 2013/0194540 A1 | 8/2013 | Pugh | |

(Continued)

FOREIGN PATENT DOCUMENTS

| | | |
|---|---|---|
| WO | 2006015315 | 2/2006 |
| WO | 2006015315 A2 | 2/2006 |
| WO | 2019162645 | 8/2019 |

OTHER PUBLICATIONS

Shim SY, Gong S, Rosenblatt MI, Palanker D, Al-Qahtani A, Sun MG, Zhou Q, Kanu L, Chau F, Yu CQ. Feasibility of Intraocular Projection for Treatment of Intractable Corneal Opacity. Cornea. Apr. 2019;38(4):523-527. doi: 10.1097/ICO.0000000000001852. PMID: 30664047; PMCID: PMC6407816. (Year: 2019).*

(Continued)

*Primary Examiner* — Eric F Winakur
*Assistant Examiner* — Emily C Clement
(74) *Attorney, Agent, or Firm* — Fish IP Law, LLP

(57) ABSTRACT

The present invention provides methods of utilizing a cranial implant to improve a mental, physical, physiological, and/or informational condition of a person. The method generally comprises steps of 1) obtaining signals from the cranial implant of the person, 2) processing the obtained signals to produce a visually renderable image, and 3) rendering the image on an intraocular display.

6 Claims, 2 Drawing Sheets

(56) References Cited

U.S. PATENT DOCUMENTS

| | | | |
|---|---|---|---|
| 2014/0316192 A1* | 10/2014 | de Zambotti | A61B 5/486 600/27 |
| 2015/0079560 A1* | 3/2015 | Cowan | A61B 5/742 600/545 |
| 2017/0075414 A1 | 3/2017 | Grant | |
| 2018/0153429 A1 | 6/2018 | Hua | |
| 2019/0099582 A1* | 4/2019 | Crow | A61B 5/01 |
| 2019/0121356 A1* | 4/2019 | Migneco | A61B 5/746 |
| 2020/0297270 A1 | 9/2020 | Ando | |

OTHER PUBLICATIONS

"Your brain with a migraine: Effect of electric currents," ScienceDaily. 5 pages.

Milikovsky, et el. "Electrocorticographic Dynamics as a Novel Biomarker in Five Models of Epileptogenesis," The Journal of Neuroscience, Apr. 26, 2017 • 37(17):4450-4461. 12 pages.

"Electroencephalogram," MayfieldClinic.com. 2 pages.

Li, et al. "Emotion classification based on brain wave: a survey," Hum. Cent. Comput. Inf. Sci. (2019) 9:42. 17 pages.

Liu, et al. "Improving Driver Alertness through Music Selection Using a Mobile EEG to Detect Brainwaves," Sensors 2013, 13, 8199-8221 23 pages.

Improving driver alertness through music selection, Lie et al., Sensors, 2013; 23 pages.

Electroencephalogram (EEG), Mayfield Clinic, Apr. 2018; 2 pages.

Your brain with a migraine effect of electric currents, ScienceDaily, Jun. 27, 2018; 5 pages.

Emotion classification based on brain wave: a survey, Li et al., Hum. Cent. Comput. Inf. Sci., 2019; 17 pages.

Dan Z. Milikovsky et al, "Electrocorticographic Dynamics as a Novel Biomarker in Five Models of Epileptogenesis", The Journal of Neuroscience, 2017; 37 (17): 4450 DOI: 10.1523/JNEUROSCI. 2446-16.2017); 12 pages.

* cited by examiner

CRANIAL IMPLANT

The field of the invention is cranial implants.

BACKGROUND

The following description includes information that may be useful in understanding the present invention. It is not an admission that any of the information provided herein is prior art or relevant to the presently claimed invention, or that any publication specifically or implicitly referenced is prior art.

There are many situations in which it can be helpful for an individual to have some external devices (a) identify an undesirable emotional, physical, and/or physiological condition, and then (b) provide a remedy. For example, it might well happen that an automobile driver is becoming drowsy, but the driver is not sufficiently aware of his/her own condition to either get off the road, or do something to alleviate the drowsiness.

Brainwaves can be used to detect drowsiness (See e.g., "Improving driver alertness through music selection, Lie et al., Sensors, 2013"), but typically a bulky electroencephalogram (EEG) machine would be completely impractical for an ordinary driver. One could alternatively employ a cranial implant to detect drowsiness, and one could perhaps then use a smart-phone app to couple to the cranial implant, and play music that might alleviate drowsiness. But in addition to having such an implant, the driver would then need to have an appropriate app loaded on the phone, the phone would have to be charged and working, and the driver would have to have enough self-awareness to use the app.

Conditions other than drowsiness can also be detected using brainwaves. For example, brainwaves can be used to detect dizziness and nausea ("Electroencephalogram (EEG), Mayfield Clinic, April, 2018"), as well as migraine-auras ("Your brain with a migraine effect of electric currents, ScienceDaily, Jun. 27, 2018"). Brainwaves can even be used to detect physical motions of a person (Emotion classification based on brain wave: a survey, Li et al., Hum. Cent. Comput. Inf. Sci., 2019"). Still further, brainwaves can be used to detect aura of epilepsy (Dan Z. Milikovsky et al, "Electrocorticographic Dynamics as a Novel Biomarker in Five Models of Epileptogenesis", The Journal of Neuroscience, 2017; 37 (17): 4450 DOI: 10.1523/JNEUROSCI.2446-16.2017).

Some of the critical components are known in the prior art, but not for the claimed methods. US20180153429A1 to Hua describes cranial implants that can be used to monitor brainwaves, including those associated with epilepsy.

U.S. Pat. Nos. 9,662,199 and 10,299,912, both to Robert Grant, describe an intra-optic lens having electronics for receiving and transmitting data, a digital display, a processor, memory, and an inductively charged power source. US patent application 2017/0075414, also to Grant, describes an implantable/wearable device for detecting diverse anatomical/physiological data. WO 2006/015315 to Feldon describes a digital display positioned on an intraocular lens. US 2013/0194540 to Pugh describes antennas and antenna systems configured into ophthalmic devices, including contact lenses. US20100234942A1 (Peyman) describes intraocular lenses having pigment that can be adjusted automatically by the intensity of the external light, or by electrical stimulation.

These and all other publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The problem with all of these technologies, however, is practicality. What is needed are methods and technologies that can monitor a person's emotional, physical, and/or physiological conditions, and then provide guidance, while always being both present and non-obtrusive.

SUMMARY OF THE INVENTION

The inventive subject matter comprises systems and methods of utilizing a cranial implant, in conjunction with an intraocular display, to improve a mental, physical, physiological, and/or informational condition of a person. Preferred embodiments include the steps of:

1) obtaining signals from the cranial implant of the person;
2) processing the obtained signals to produce a visually renderable image; and
3) rendering the image on an intraocular display.

All signals that can realistically be obtained by a cranial implant are contemplated. For example, a cranial implant might well detect brainwaves, auditory vibrations, electrical signals moving along an optic nerve, body or external temperatures, blood pressure, and sugar level or other chemical concentration in the blood. Cranial implants can obtain these signals directly from onboard sensors, or indirectly from sensors located outside the implant.

Signals obtained by a cranial implant can be interpreted in any useful manner, including for example, to determine emotional and other mental conditions, intent, and physical or physiological conditions. As used herein, the term "mental conditions" include positive, negative, and neutral emotional conditions. Also as used herein, the term "physical conditions" refers to biological structures, while "physiological conditions" refers to biological functions.

Processing of signals obtained from a cranial implant can be accomplished in any suitable manner, within or without the confines of a person. For example, processing could take place on a cell phone carried by a person in which the cranial implant is implanted, with communication between the implant and the cell phone carries out by Bluetooth or other communication protocol. Processing could alternatively or additionally take place on a processor located within the body, such as within an intraocular device that includes the intraocular display.

Rendering an image on an intraocular display will depend upon what signals are obtained from the implant, what outcome is desired, and what image or images could advantageously be rendered to try to achieve that outcome. Contemplated desirable outcomes include improvements in mental, physical, physiological, and/or informational condition of a person.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Figure 1:
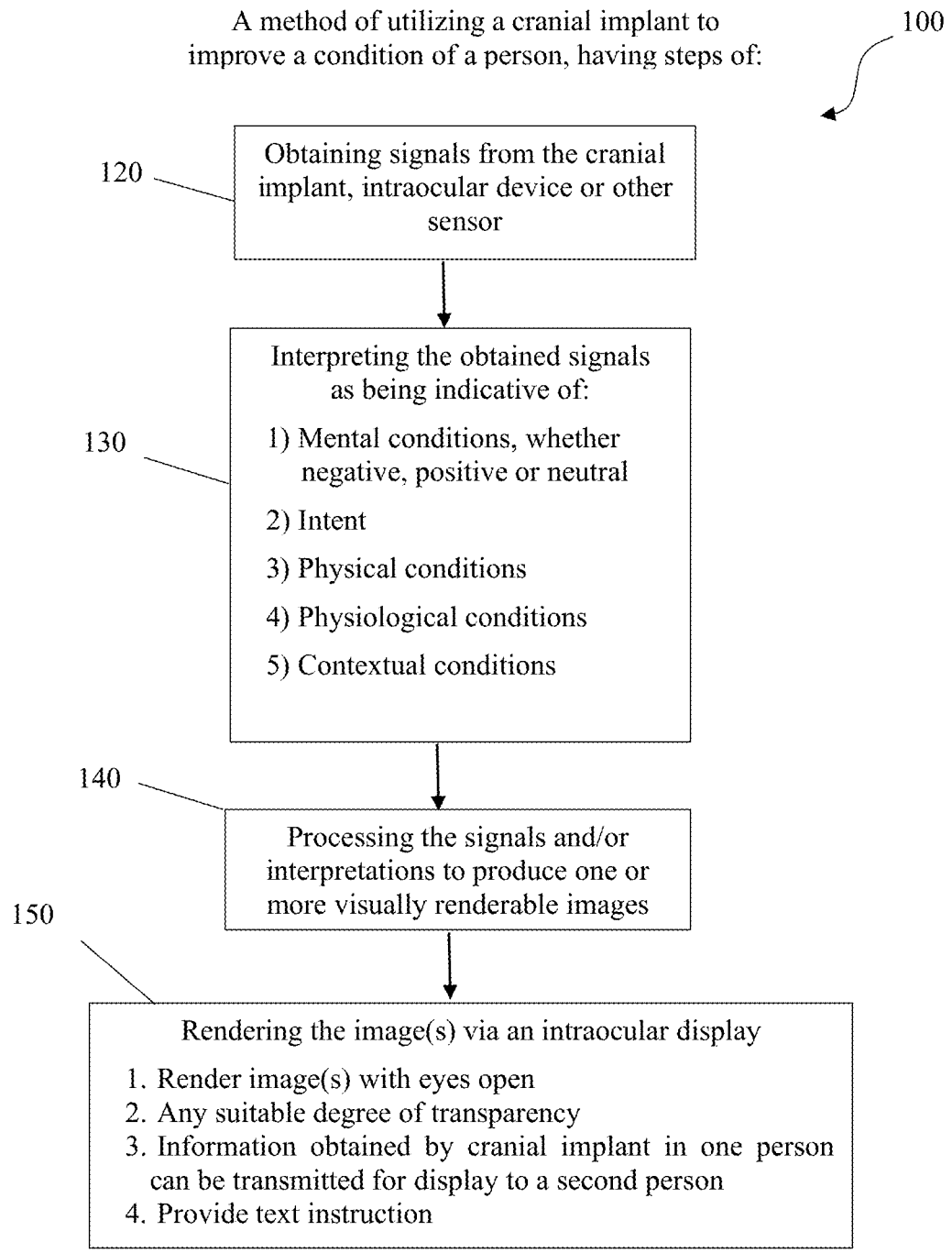
FIG. 1 is a schematic depiction of a method of utilizing a cranial implant to improve a mental, physical, physiological, and/or informational condition of a person.

FIG. 1 is a schematic depiction of a method 100 to improve a mental, physical, physiological, and/or informational condition of a person. The method generally comprises: step 120, obtaining signals from a intraocular device or other sensor, step 130 interpreting the obtained signal as indicative of mental conditions, intent, physical conditions, physiological conditions, or contextual conditions, step 140 processing the signals and/or interpretations to produce one or more visually renderable images, and step 150 rendering the image(s) via an intraocular display At step 120 All signals that can realistically be obtained by a cranial implant, can be used in method 100. For example, a cranial implant might well detect brainwaves, auditory vibrations, electrical signals moving along an optic nerve, body or external temperatures, blood pressure, and sugar level or other chemical concentration in the blood. Cranial implants can also obtain any of these, or other signals, from sensors located outside the implant.

As used herein, the term "cranial implant" means a sensor positioned somewhere on the head of a person. Cranial implants can be located supra- or sub-dermal, or within the cranium, or extend across one or more of those domains. Also as used herein, the term "brainwaves" includes, but is not limited to, waves typically grouped according to predominant frequencies, Delta (0.5 TO 3 Hz), Theta (3 TO 8 HZ), Alpha (8 TO 12 HZ), Beta (12 TO 38 HZ), or Gamma (38 TO 42 HZ) waves.

In step 130, signals obtained from the cranial implant can be interpreted in any useful manner, including for example, as an emotional condition, a neutral mental condition, an intent, physical condition, normal or abnormal physiological condition, or contextual conditions.

In step 140, obtained signals are processed to produce a visually renderable image. In most cases suitable images can be obtained from a local or distal data store of stock images, or can be created on the fly as text messages display on the intraocular device. The next several paragraphs provide examples and other guidance as to how obtained signals can be interpreted, and how the signals and/or interpretations can be processed to produce one or more visually renderable images In some embodiments, brainwaves can be associated with desired emotional conditions, and improvements in emotional, physical, and/or physiological conditions can be accomplished by rendering appropriate therapeutic or informational images. For example, an emotional condition of depression could conceivably be ameliorated by displaying a beautiful nature scene, or other therapeutic images, on an intraocular display. Depression could also conceivably be ameliorated by displaying an informational image that includes inspirational message, or guidance to engage in exercise. Other emotional conditions that could be used to trigger rendering of therapeutic or informational images include fear, anger, disgust, sadness, rage, loneliness, melancholy, and annoyance.

Rendering of therapeutic or informational images by an intraocular display need not, however, be triggered by negative emotional conditions. For example, brainwaves associated with a happy or joyful condition could be used to trigger informational images about fun baking projects, or images of friends that a person might want to contact.

Methods contemplated herein can also be used to render images related to mental conditions that are emotionally neutral. For example, a person could concentrating on a math problem, or mixing ingredients to prepare a meal. In such cases brainwaves associated with concentration might be used to render a light green, pink, or other relaxing color filter on an intraocular display, which might thereby improve the person's ability to concentrate.

Emotionally neutral mental conditions can also include some types of intent. For example, a brainwave pattern might be associated with a person intending to go outside. In such instances, an intraocular display might advantageously render an image of car or office keys, or a coronavirus mask, to help a person remember to bring those items. Whatever system is processing the obtained signals might also be used to obtain weather or information from an external source, and send that information to the intraocular display.

Still further, brainwaves could detect abnormal physiological conditions. For example, a person's brainwaves could indicate an abnormal condition of drowsiness, and an intraocular display could be used to render bright lights, or informational or instructional messages such as "wake up!", "driving is dangerous!", or "rest stop in 2 miles". In an other example, a person's brainwaves could indicate an epileptic aura, and either the brainwaves or the cranial implant might detect that the aura is associated with a blinking light. In such cases an intraocular display could be used to block vision of the blinking lights, thereby possibly preventing or mitigating an epileptic seizure.

As mentioned above, a cranial implant can be used to obtain signals other than brainwaves. Contemplated signals include physiological conditions such as blood pressure, and concentrations of blood sugar or other blood chemicals. These signals can be detected directly, using a sensor on the cranial implant, or indirectly using a sensor elsewhere on a person's body, with data transmitted to the cranial implant, processor, or other component of the device. Contemplated information derived from such signals, and rendered on an intraocular display includes parameter values (e.g., 120/80 blood pressure, 120 mg/dL blood sugar), and instructional information such as "lie down to reduce blood pressure" or "did take your medication?".

Sensors other than brainwave sensors could also be used to detect physical (i.e., anatomic) conditions. For example, sensors could be positioned on a limb of a person who cannot consciously move the limb. Accordingly, where it appears that the limb has not been moved in a long period of time, systems and methods contemplated herein might be used to display on an intraocular display, an instruction to contact a helper to move the limb, or images of a helper moving the limb.

Cranial implant or other sensors can also be used to obtain information about a current context of or about the person. For example, a cranial implant could have a UV sensor, and UV intensity or cumulated UV exposure obtained from that sensor could be used to render that information on an intraocular display, "you've been out in the sun too long" or "use sun block". In another example, a cranial implant could detect ambient temperature, and that information could be used in combination with hydration information from a sensor, and an intraocular display, to warn a person to drink fluids. In yet another example, a cranial implant could detect ambient sounds, including voices and car sounds, and render text or information regarding such sounds to a deaf person using intraocular display. In yet another example, a cranial implant could have a magnetic directional sensor, or even a GPS, and corresponding information could be used to render position or direction information using an intraocular display.

Context sensors can be used in concert with an intraocular display to provide a person with an augmented reality experience. For example, sensors could indicate that a person is thinking about a dog while lying on a bed, and the intraocular display could provide a partially transparent image of a dog laying down on the bed, alongside the person. Similarly, when the person is running, the rendered augmented reality image could be of a dog running alongside. Another example is that when a first sensor detects that a person is walking, and a second sensor detects that sound of a bird singing, the intraocular display could render an image of a flying bird that corresponds with the bird sounds.

In step 150, one or more images are rendered to a user via an intraocular display. Contemplated intraocular displays can include those found in the prior art discussed above.

Contemplated intraocular displays can have any suitable degree of transparency. Completely opaque displays can be useful in blocking ambient images from entering a user's eye, and partially transparent displays can be useful in superimposing an image upon a current visual field.

It is contemplated that an intraocular display can be used even when the eyes are closed. For example, a cranial implant could detect brainwaves associated with a person trying to fall asleep, and an intraocular display could render a soft calming color, even when the person's eyes are closed. A cranial implant might also have a position sensor, which detects that the person has been lying down for a given time, and therefore trigger an intraocular display to render an image that would help the person sleep.

It also contemplated that an image associated with signals obtained from a cranial implant in a first person could be transmitted for display to a second person. The information might or might not be displayed in an intraocular device of the second person. In one example, such a system could be used for enabling a nurse to see information on his/her intraocular display, which is transmitted from a patient's cranial implant.

In some instances, the renderable image can include an instruction to the person. For example, when the migraine-aura is detected from the signals, the image includes an instruction to take a drug to mitigate the upcoming migraine condition. The amount of the drug in the instruction can depends on the level of the aura detected by the signals.

In some embodiments, when an undesired emotional condition is detected through brainwaves or other indications identified by one or more sensors, image can be rendered on the intraocular display that are targeted to producing a desired emotional condition. For example, when the brainwaves are deemed to be indicative of sadness, rendered images might be beautiful flowers or delicious foods. Rendered images can be white and black, or any combination of renderable colors.

Figure 2:
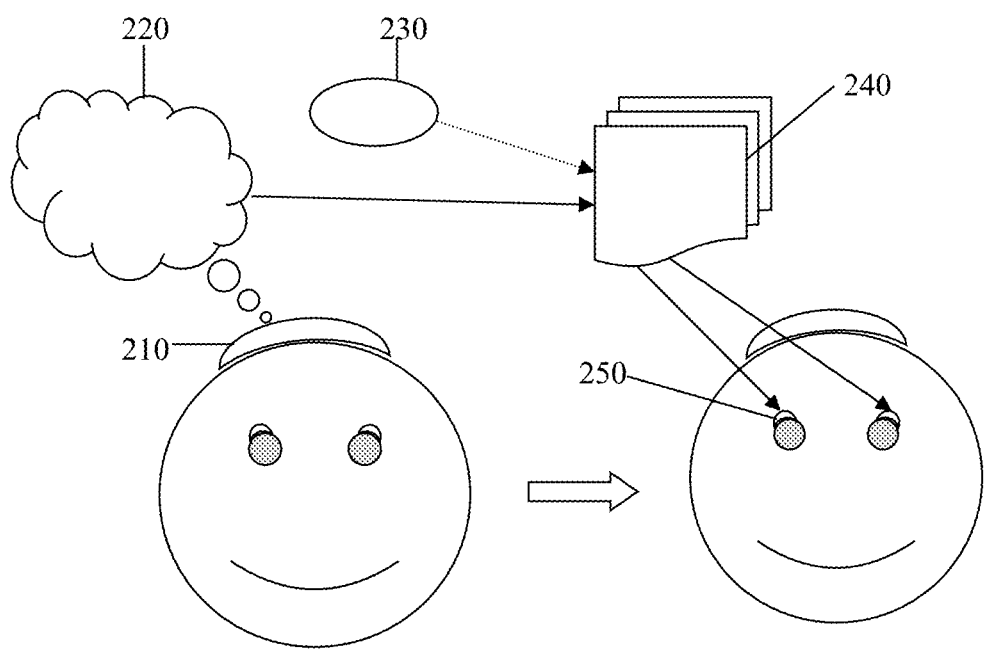
FIG. 2 is a schematic depiction of information being rendered by an intraocular display improve a mental, physical, physiological, and/or informational condition of a person.

FIG. 2 is a schematic depiction of information 240, being rendered by an intraocular display 250, to improve a mental, physical, physiological, and/or informational condition of a person. As described above, the method generally comprises (1) obtaining one or more signals 220, from a cranial implant 210, (2) optionally obtaining one ore more signals from sensors other than associated with the cranial implant 230, (3) interpreting/processing the obtained signals to produce one or more visually renderable images 240, and (4) rendering the image(s) 240 on an intraocular display 250.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of utilizing a cranial implant to improve a mental, physical, physiological, and/or informational condition of a person, comprising:

obtaining a signal from the cranial implant of the person associated with the person trying to go to sleep;

obtaining a second signal from a position sensor that is indicative of the person lying down for a predetermined amount of time;

processing the obtained signals to produce a visually renderable image based on the signal from the cranial implant and the signal indicating the person has been lying down for the predetermined amount of time; and rendering the image on an intraocular display such that the image is visible to the person while the person's eyes are closed, the image comprising an image that assists the person in falling asleep, wherein the image is rendered in a calming color.

2. The method of claim 1, wherein the signal obtained from the cranial implant comprises a signal indicative of at least one of a mental condition of the person, an intent of the person, a physical condition of the person, a physiological condition of the person, and a contextual condition of the person.

3. The method of claim 1, wherein the cranial implant senses brainwaves of the person, and further comprising producing different images as a function of whether the brainwaves predominantly include Delta (0.5 TO 3 Hz), Theta (3 TO 8 HZ), Alpha (8 TO 12 HZ), Beta (12 TO 38 HZ), or Gamma (38 TO 42 HZ) waves.

4. The method of claim 1, wherein the intraocular display is partially transparent.

5. The method of claim 1, further comprising obtaining second signals from a second cranial implant in a second person, and rendering a second image on the intraocular display.

6. The method of claim 1, wherein the image comprises a combination of colors.

\* \* \* \* \*